United States Patent [19]

Saulnier et al.

[11] Patent Number: 4,868,291

[45] Date of Patent: Sep. 19, 1989

[54] 4'-DESHYDROXYEPIPODOPHYLLOTOXIN GLUCOSIDES: SYNTHESIS AND USE

[75] Inventors: Mark G. Saulnier, Middlesex; Dolatrai M. Vyas, Madison, both of Conn.

[73] Assignee: Bristol-Myers Company, New York, N.Y.

[21] Appl. No.: 87,355

[22] Filed: Aug. 20, 1987

[51] Int. Cl.$^4$ .................. C07D 21/00; C07H 15/24
[52] U.S. Cl. .................. 536/18.1; 536/17.2; 536/18.2; 536/4.1; 514/908
[58] Field of Search .................. 536/18.1, 18.2, 17.2, 536/4.1; 514/33, 35, 908

[56] References Cited

U.S. PATENT DOCUMENTS

| | | | |
|---|---|---|---|
| 608,815 | 11/1960 | Kussmaul et al. | 536/18.1 |
| 3,408,441 | 10/1968 | Wartburg et al. | 536/18.1 |
| 3,524,844 | 8/1970 | Keller-Juslen et al. | 536/18.1 |
| 4,547,567 | 10/1985 | Umezawa et al. | 536/18.1 |
| 4,609,644 | 9/1986 | Nemec | 536/18.1 |
| 4,757,138 | 7/1988 | Fujii et al. | 536/4.1 |

FOREIGN PATENT DOCUMENTS

| | | | |
|---|---|---|---|
| 0141057 | 5/1985 | European Pat. Off. | 536/18.1 |
| 0823068 | 11/1959 | United Kingdom | 536/18.1 |
| 1162248 | 8/1969 | United Kingdom | 536/18.1 |
| 86/00018 | 1/1986 | World Int. Prop. O. | 536/18.1 |

OTHER PUBLICATIONS

Haim et al; Biochem. Biophys. Res. Commun., 135:215–220, Feb. 1986.

J. Med. Chem., 14 (10):936–940 (1971); Keller-Juslén et al.

Proc. Am. Assoc. Cancer Res., 24: 319 (1983); Maanen et al; No. 1262.

American Society for Pharmacology and Experimental Therapeutics Meetings, Boston, MA, Aug. 18–22, 1985; Haim, N.; Nemec, J.; Roman, J.; Sinha, B. K.; "Etoposide Activation by Liver Microsomes".

J. Electroanal. Chem., 184: 317–329 (1985); Holthuis et al.

Biochemistry, 23: 1183–1188 (1984); Long et al.

*Primary Examiner*—Ronald W. Griffin
*Assistant Examiner*—Nancy S. Carson
*Attorney, Agent, or Firm*—David M. Morse

[57] ABSTRACT

Novel 4'-deshydroxyepipodophyllotoxin glucosides are provided as antitumor agents useful in inhibiting the growth of mammalian tumors. The invention also provides novel intermediates and processes for the preparation of the 4'-deshydroxyepipodophyllotoxin glucoside end-products. A preferred embodiment is 4'-deshydroxyetoposide.

12 Claims, No Drawings

4'-DESHYDROXYEPIPODOPHYLLOTOXIN GLUCOSIDES: SYNTHESIS AND USE

BACKGROUND OF THE INVENTION

1. Field of the Invention

The present invention is directed to novel 4'-deshydroxyepipodophyllotoxin glucosides, to methods of preparing these new compounds, and to the therapeutic use of the compounds in inhibiting the growth of mammalian tumors.

2. Description of the Prior Art

Etoposide (VP-16, Ia) and teniposide (VM-26, Ib) are clinically useful anticancer drugs derived from the naturally occurring lignan, podophyllotoxin (II). The numbering system used for nomenclature purposes is shown in Formula II. Etoposide and teniposide are epipodophyllotoxin derivatives; epipodophyllotoxin being the epimer of podophyllotoxin at the 4-position. Etoposide and teniposide are active in the treatment of a variety of cancers including small cell lung cancer, non-lymphocytic leukemia and non-seminomatous testicular cancer.

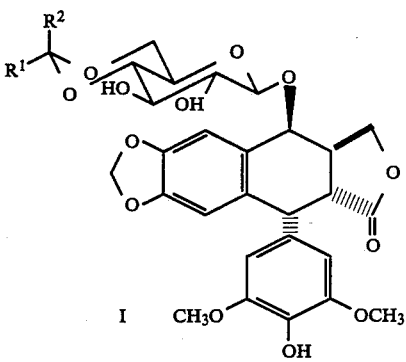

I

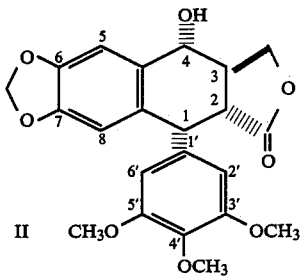

II

Ia $R^1 = CH_3$, $R^2 = H$
Ib $R^1 = $ 2-thienyl, $R^2 = H$

Etoposide and teniposide and methods for their preparation are disclosed in U.S. Pat. No. 3,524,844 and *J. Med. Chem.* 14 (10): 936–940, 1971. Encompassed by the above-mentioned references are compounds of formula I above in which $R^2$ is hydrogen and $R^1$ is selected from the group consisting of $C_1$–$C_{10}$ alkyl, $C_2$–$C_{10}$ alkenyl, $C_3$–$C_7$ cycloalkyl, furyl, thienyl, pyridyl, pyrrolyl, $C_6$–$C_{10}$ aryl and $C_7$–$C_{14}$ aralkyl, said aryl and aralkyl rings optionally bearing one or more substituents selected from halo, $C_1$–$C_4$ alkyl, nitro, hydroxy, $C_1$–$C_4$ alkoxy, $C_1$–$C_4$ alkanoyloxy, cyano, amino, $C_1$–$C_4$ alkylamino, di($C_1$–$C_4$)alkylamino, carboxy, $C_1$–$C_4$ alkylthio, mercapto, $C_2$–$C_4$ alkenoylamino, $C_1$–$C_4$ alkanoyl, $C_2$–$C_4$ alkenyl and carbamoyl; or $R^1$ and $R^2$ are each $C_1$–$C_{10}$ alkyl; or $R^1$ and $R^2$ and the carbon atom to which they are attached join to form a $C_5$–$C_6$ cycloalkyl group.

The etoposide 3',4'-orthoquinone IIIa shown below is derived from the oxidation of etoposide as described in U.S. Pat. No. 4,609,644. This quinone IIIa has been implicated as a reactive intermediate in the metabolic activation of etoposide by rat liver and hela microsomal fractions (*Proc. Am. Assoc. Cancer Res.* 24, 319, 1983) and also has been suggested as a bioalkylating agent in a report describing the metabolism of etoposide by mouse liver microsomes (see Haim, N; Nemec, J.; Roman, J.; Sinha, B. K. presented at the *American Society for Pharmacology and Experimental Therapeutics meetings* at Boston, MA, Aug. 18–22, 1985). In addition the peroxidative activation of etoposide or teniposide has been shown to result in the formation of two metabolites, one of which has been identified as the corresponding orthoquinone III (see Haim, N.; Roman, J.; Nemec, J.; Sinha, B. K. *Biochemical and Biophysical Research Communications* 135, 215, 1986). These same authors have shown that the peroxidative activation of these drugs produces phenoxy radical intermediates and propose that concomitant O-demethylation to the orthoquinone of formula III may be important in the mechanism of action of etoposide and teniposide. Etoposide 3',4'-orthoquinone IIIa has been generated, isolated and characterized from the electrochemical oxidation of etoposide (see *J. Electroanal. Chem.* 184: 317, 1985).

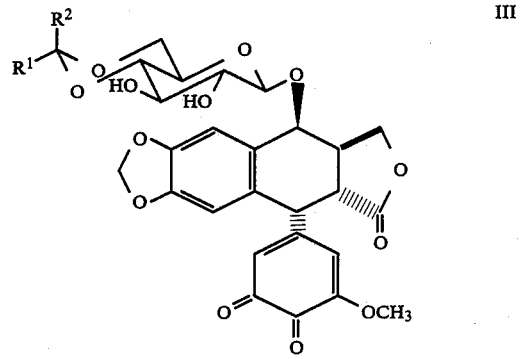

IIIa, $R^1 = CH_3$, $R^2 = H$

The 4'-deshydroxyetoposide analog IVa would be incapable of producing the 3',4'-ortho-quinone IIIa, and thus any biological activity attributed to it would most likely be due to an alternative mechanism of action such as inhibition of DNA topoisomerase II. Moreover, since a free hydroxyl group at the 4'-position of etoposide and teniposide has been regarded as essential for DNA breakage activity (see *Biochemistry* 23: 1183, 1984), the corresponding 4'-deshydroxy analog would not be expected to cause DNA strand cleavage and thus should show little or no antitumor activity in-vitro and in-vivo.

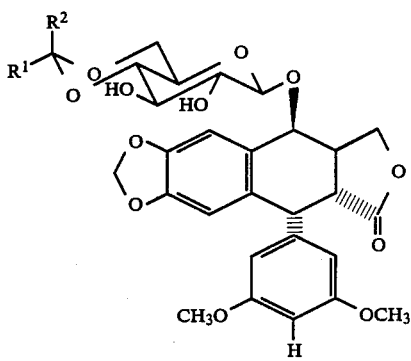

IVa, $R^1$ = $CH_3$, $R^2$ = H
IVb, $R^1$ = 2-thienyl, $R^2$ = H

Surprisingly, we have prepared the 4'-deshydroxy compounds of formula IV and have shown them to have significant antitumor activity both in-vitro and in-vivo against various tumor systems.

SUMMARY OF THE INVENTION

The present invention relates to 4'-deshydroxyepipodophyllotoxin derivatives of formula IV

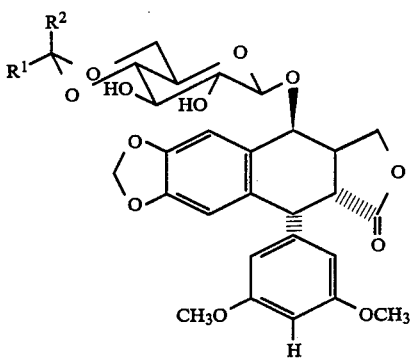

wherein $R^2$ is hydrogen and $R^1$ is selected from the group consisting of $C_1$–$C_{10}$ alkyl, $C_2$–$C_{10}$ alkenyl, $C_3$–$C_7$ cycloalkyl, furyl, thienyl, pyridyl, pyrrolyl, $C_6$–$C_{10}$ aryl and $C_7$–$C_{14}$ aralkyl, said aryl and aralkyl rings optionally bearing one or more substituents selected from halo, $C_1$–$C_4$ alkyl, nitro, hydroxy, $C_1$–$C_4$ alkoxy, $C_1$–$C_4$ alkanoyloxy, cyano, amino, $C_1$–$C_4$ alkylamino, di($C_1$–$C_4$)alkylamino, carboxy, $C_1$–$C_4$ alkylthio, mercapto, $C_2$–$C_4$ alkenoylamino, $C_1$–$C_4$ alkanoyl, $C_2$–$C_4$ alkenyl and carbamoyl; or $R^1$ and $R^2$ are each $C_1$–$C_{10}$ alkyl; or $R^1$ and $R^2$ and the carbon atom to which they are attached join to form a $C_5$–$C_6$ cycloalkyl group.

In another aspect the present invention provides novel intermediates useful in the preparation of the end-products of formula IV, said intermediates having the formulae

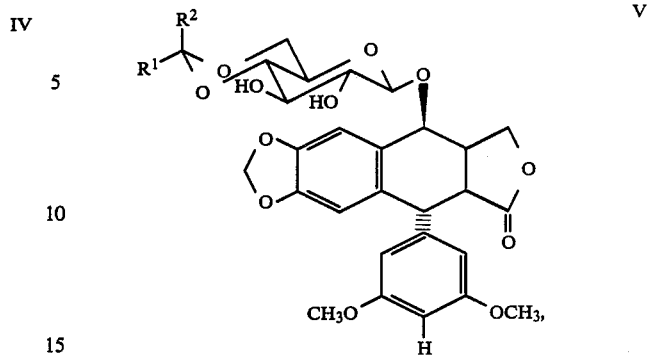

which are the cis or picro lactone isomers of the compounds of formula IV,

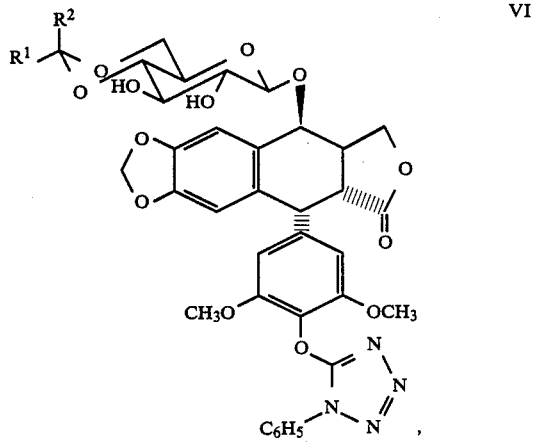

which are the corresponding 4'-(1-phenyl-1H-tetrazol-5-yl)ethers of the compounds of formula IV, and

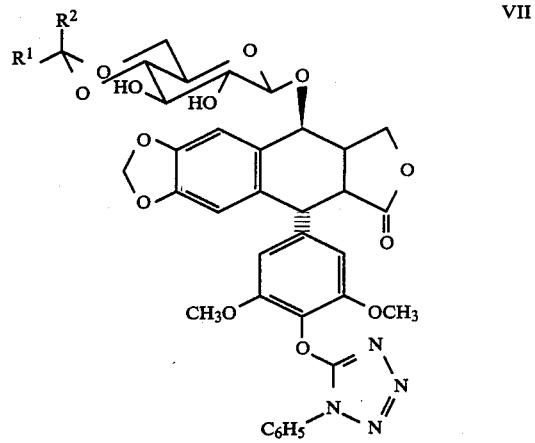

which are the corresponding 4'-(1-phenyl-1H-tetrazol-5-yl)ethers of the intermediates of formula V, wherein $R^1$ and $R^2$ in the above formulae V, VI, and VII are as defined for formula IV.

In yet another aspect the present invention provides a pharmaceutical composition comprising an effective tumor-inhibiting amount of a compound of formula IV and a pharmaceutically acceptable carrier.

In still another aspect the present invention provides a method for inhibiting tumors in a mammalian host which comprises administering to said host a tumor-inhibiting amount of a compound of formula IV, or a pharmaceutical composition thereof.

DETAILED DESCRIPTION OF THE INVENTION

The compounds IV of the present invention are prepared from starting materials of general formula I shown above. These compounds are known in the literature as evidenced by U.S. Pat. No. 3,524,844 and *J. Med. Chem.* 14 (10): 936–940, 1971. The preferred starting materials of formula I, and thus the preferred compounds of formulae IV, V, VI and VII, are those wherein $R^2$ is hydrogen and $R^1$ is $C_1$–$C_{10}$ alkyl, most preferably $C_1$–$C_8$ alkyl; $C_2$–$C_{10}$ alkenyl, most preferably $C_2$–$C_8$ alkehyl; $C_5$–$C_6$ cycloalkyl; 2-furyl; 2-thenyl; and phenyl, phenyl($C_1$–$C_4$) alkyl; or phenyl($C_2$–$C_4$-alkenyl) radicals wherein the phenyl ring may be mono- or di-substituted by one or more substituents selected from halo (chloro, bromo, iodo, fluoro), $C_1$–$C_4$ alkyl, $C_1$–$C_4$ alkoxy, hydroxy, nitro and amino.

The most preferred starting materials of formula I, and hence most preferred compounds of formulae IV—VII, are those wherein $R^2$ is hydrogen and $R^1$ is $C_1$–$C_{10}$ alkyl, more preferably $C_1$–$C_6$ alkyl and most preferably methyl; phenyl; or 2-thienyl. The most preferred embodiment comprises compounds where $R^2$ is hydrogen and $R^1$ is methyl, i.e. the starting material is etoposide.

The compounds of formula IV may be prepared by the following reaction scheme:

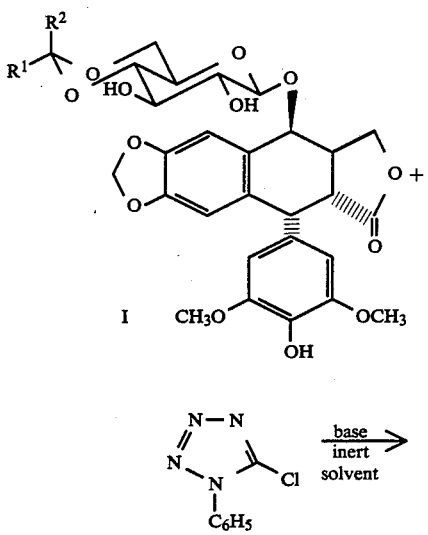

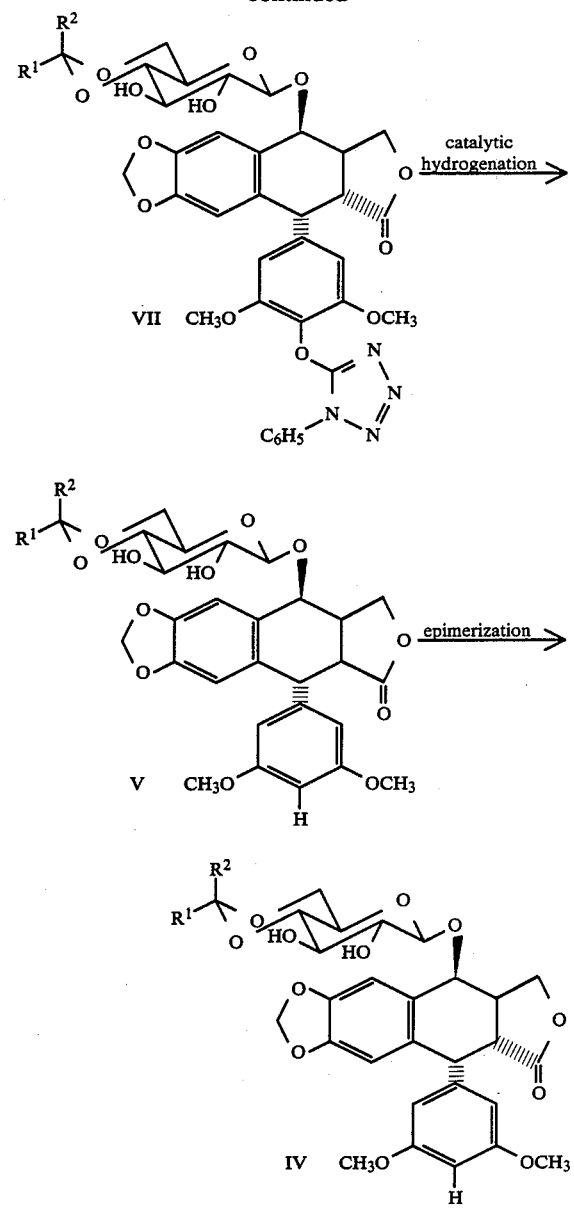

Alternatively, intermediate VII may be epimerized to give the corresponding trans lactone ether of formula VI which can then be cleaved by catalytic hydrogenation to give the desired end-product IV.

To elaborate, the starting material of formula I is alkylated in an inert solvent with 5-chloro-1-phenyl-1H-tetrazole in the presence of base and, following concomitant epimerizaton, the thermodynamically more stable cis (picro) lactone isomer of formula VII is produced. Despite varying the reaction conditions it was not possible to achieve only the alkylation reaction to produce the desired trans isomer ether of formula VI. The alkylation is carried out by reacting the starting material I and tetrazole reactant in approximately molar equivalent amounts or with a slight excess of tetrazole in an inert solvent, preferably an inert anhydrous organic solvent such as methyl ethyl ketone, dimethylformamide or a mixture thereof. A mild base such as potassium carbonate is employed and the reaction is preferably conducted with heating, e.g. at reflux, under an inert atmosphere.

The picro lactone ether VII may be epimerized to the desired trans lactone either which can then be cleaved by catalytic hydrogenation to give bioactive compound IV or, alternatively, the ether VII may be catalytically hydrogenated to give the picro lactone intermediate V which can then be epimerized to the desired end-product IV.

Catalytic hydrogenation of ether VI or VII is carried out employing a hydrogenation catalyst such as palladium which is optionally supported on a conventional carrier such as carbon in a nonreducible inert solvent such as ethyl acetate or methanol, or mixtures of such inert solvents. Hydrogenation is best conducted in a bomb apparatus at high pressures (e.g. 1000–1100 psi/$H_2$) at elevated temperatures of about 80°–100° C.

The picro lactone intermediate V resulting from catalytic hydrogenation of either VII or the picro lactone ether intermediate resulting from alkylation of starting material I may be epimerized to the desired trans lactone isomer by reacting the picro isomer in an inert organic solvent such as tetrahydrofuran at a low temperature (−78° C. to −40° C.), preferably at about −78° C., while employing a strong base such as potassium bis(trimethylsilyl)amide, lithium diisopropylamide (LDA) or lithium bis(trimethylsilyl)amide. The resulting anion is then quenched with acid, e.g. (1)-tartaric acid, acetic acid, etc., to produce the corresponding trans lactone isomer. The epimerization reaction results in a mixture of picro and trans isomers which are separable by conventional procedures, e.g. HPLC or preparative TLC, to give the pure trans isomer.

BIOLOGICAL ACTIVITY

The compound of Example 4 was evaluated for its antitumor activity in an in vitro cytotoxicity assay against human and murine tumor cell lines, as well as against transplantable murine P388 leukemia.

CYTOTOXICITY ASSAY

The in vitro cytotoxicity assay involves growing various mammalian tumor cells, including human tumor cells, on Microtiter plates employing established tissue culture methods. The concentration of each compound required to inhibit cell growth by 50% ($IC_{50}$) is then determined by a four-fold serial dilution technique. The validity of the method has been supported by a report published in the "Proceedings of the American Association for Cancer Research", 1984, 25: 1891 (Abst. No. 328). Tumor cells of the following type were employed: B16-F10 murine melanoma, Moser human colon, SW900 human lung resistant to teniposide (VM) and etoposide (VP) and three human colon tumor cell lines, i.e. HCT-116, HCT-VM and HCT-VP, the latter two being resistant to teniposide (VM) and etoposide (VP), respectively. $IC_{50}$ values less than 500 mg/ml are a positive indicator of antitumor activity. Table I presents $IC_{50}$ values against the above-mentioned cell lines.

TABLE I

| | In vitro cytotoxicity assay $IC_{50}$ values (μg/ml)* | | | | |
|---|---|---|---|---|---|
| B16-F10 | HCT-116 | HCT/VM34 | HCT/VP35 | MOSER | SW900 |
| 23 | 3.0 | 3.7 | 3.3 | 60 | >125 |

TABLE I-continued

| | In vitro cytotoxicity assay $IC_{50}$ values (μg/ml)* | | | | |
|---|---|---|---|---|---|
| B16-F10 | HCT-116 | HCT/VM34 | HCT/VP35 | MOSER | SW900 |
| 27 | 11.6 | >125 | 3.5 | 31 | 51 |

*Test compound is compound of Example 4 dissolved in DMSO

P388 Leukemia

Female $CDF_1$ mice were implanted intraperitoneally with a tumor inoculum of $10^6$ ascites cells of P388 murine leukemia and treated with various doses of the compound of Example 4; four mice were used for each dose level and ten were used as saline-treated control. The compound was administered by intraperitoneal injection in two injections on day 1 and day 5. Antitumor activity was expressed as %T/C which is the ratio of the median survival time (MST) of the drug-treated group to the MST of the saline-treated control group. A compound showing a %T/C of 125 or greater is generally considered to have significant antitumor activity in the P388 test. The experiment lasted 31 days at the end of which time the number of survivors was noted. Table II shows the results of the P388 test; only the maximum %T/C and the dose showing the maximum effect are reported.

TABLE II

| Antitumor Activity against Murine P388 Leukemia | | | | |
|---|---|---|---|---|
| Compound | Dose (mg/kg/inj.) | MST (days) | % T/C | Day 5 No. mice alive/total** |
| Example 4 *Compound | 150 | 17.5 | 175 | 4/4 |
| Saline Control | 0.5 ml | 10.0 | 100 | 10/10 |

*Dissolved in water, carboxymethylcellulose and Tween-80
**At day 31 no mice were alive in either test or control group It is apparent from the results provided above that the compounds of formula IV possess effective inhibitory activity against mammalian tumors. Accordingly the present invention provides a method of inhibiting mammalian tumors which comprises administering an effective tumor-inhibiting dose of a compound of formula IV to a tumor bearing host.

Another aspect of this invention provides a pharmaceutical composition which comprises an effective tumor-inhibiting amount of an antitumor compound of formula IV and a pharmaceutically acceptable carrier. These compositions may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are for illustrative purposes only and should not be construed as limiting the scope of the invention.

In the following examples, all temperatures are given in degrees Centigrade. Melting points were recorded on a Thomas-Hoover capillary melting point apparatus and are uncorrected. Ultraviolet spectra were recorded using a Hewlett-Packard 8450 ultraviolet/visible spectrophotometer. High pressure liquid chromatography (HPLC) was carried out using a Waters Model 590 instrument. $^1$H NMR spectra were recorded on a Bruker WM 360 spectrophotometer (using CDCl$_3$ as an internal reference). Chemical shifts are reported in δ units and coupling constants in Hertz. Splitting patterns are designated as follows: s, single; d, doublet; t, triplet; q, quartet; m, multiplet; bp, broad peak; and dd, doublet of doublet. Infrared spectra were determined on a Perkin-Elmer 1800 Fourier Transform Infrared Spectrophotometer and are reported in reciprocal centimeters (cm$^{-1}$). "Flash Chromatography" refers to the method described by Still (Still, W. C. et al, J. Org. Chem., 1978, 43: 2923) and was carried out using E. Merck silica gel (230–400 mesh). Preparative thin layer chromatography using E. Merck 20×20 cm plates (60F254 Kiesel gel/0.5 mm) bearing 4×20 cm pre-concentrating zone gave the best results.

EXAMPLE 1

Picro-etoposide-4'-(1-phenyl-1H-tetrazol-5-yl)ether (VIIa)

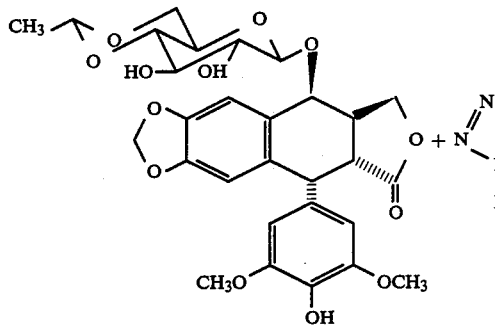

A magnetically stirred mixture of etoposide (400 mg, 0.680 mmol), 5-chloro-1-phenyl-1H-tetrazole (166.5 mg, 0.894 mmol) and anhydrous potassium carbonate (505 mg, 3.65 mmol) was treated with methyl ethyl ketone (25 ml) and anhydrous dimethylformamide (10 ml) and refluxed under N$_2$ for 19–20 h. The mixture was cooled and partitioned with water (200 ml) and ethyl acetate (2×175 ml). The combined extracts were washed with H$_2$O (2×150 ml) and brine (175 ml) and dried (Na$_2$SO$_4$/MgSO$_4$). Rotary evaporation followed by preparative TLC on silica gel gave 332.5 mg (66.8%) of the pure title compound as a white solid, mp 190°–193° C.

IR (KBr) 3455, 1768, 1603, 1546, 1507, 1483, 1464, 1421, 1339, 1252, 1130, 1037, 933, 888, 761, 689 cm$^{-1}$.

UV (CH$_3$OH) λ max (log Σ) 291 (3.613) nm.

360 MHz $^1$H NMR (CDCl$_3$) δ 7.87 (d, 2H), 7.58–7.45 (m, 3H), 6.81 (s, 1H), 6.51 (s, 2H), 6.45 (s, 1H), 5.97 (d, 2H), 4.92 (d, 1H), 4.73 (q, 1H), 4.56–4.42 (m, 2H), 4.31 (d, 1H), 4.18 (dd, 1H), 3.95 (d, 1H), 3.76 (s, 6H), 3.62–3.55 (m, 2H), 3.47–3.40 (m, 1H), 3.32 (dd, 1H), 3.21–3.12 (m, 2H), 3.05–2.96 (m, 1H), 2.90 (d, 1H, OH), 2.76 (d, 1H, OH), 1.33 (d, 3H).

mass spectrum (FAB), m/e, 733.2393 (M$^+$+H). C$_{36}$H$_{37}$N$_4$O$_{13}$ requires 733.2357.

EXAMPLE 2

Picro-4'-desmethoxyetoposide (Va)

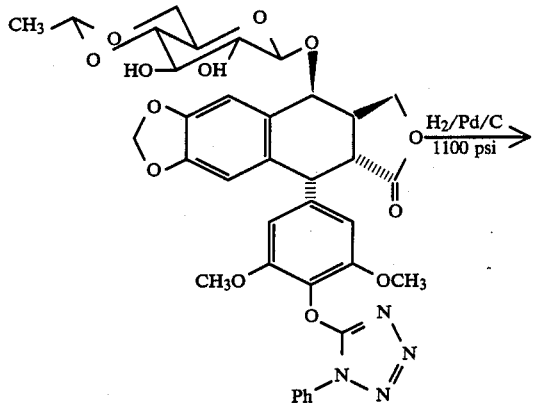

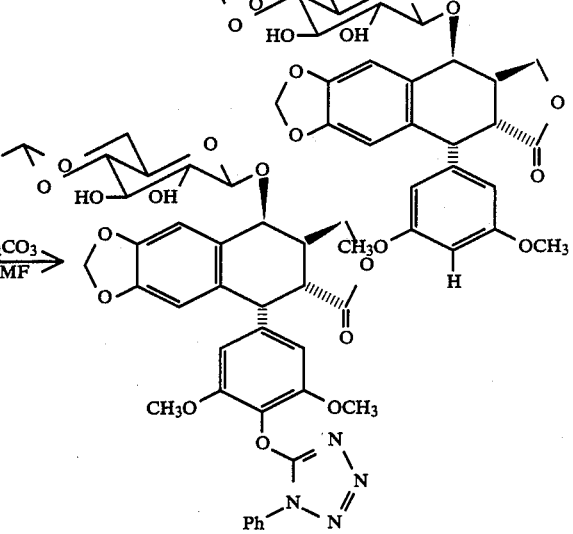

A solution of the picro-etoposide-4'-tetrazole ether (470 mg, 0.642 mmol; prepared as described in Example 1) in ethyl acetate (14 ml) and methanol (4 ml) was treated with 20% Pd(OH)₂ on carbon (300 mg) and hydrogenated in a bomb apparatus at 1050–1100 psi/H₂ at 80°–100° C. for 21 h. The mixture was cooled, filtered through Celite, and the solids were washed with excess ethyl acetate. The filtrate was evaporated in vacuo and the residue was purified by flash chromarography on silica gel using 2% CH₃OH/EtOAc to give 212.3 mg (58%) of pure picro-4'-desmethoxyetoposide as a colorless solid. Further elution with 4% CH₃OH/EtOAc provided 170 mg of picro-etoposide. Data for picro-4'-desmethoxyetoposide: mp 134°–136° C.

IR (KBr) 3480, 3450, 1767, 1600, 1485, 1430, 1383, 1259, 1207, 1160, 1080, 1040, 1014, 935, 890, 837 cm⁻¹.

UV (CH₃OH) max (log Σ) 284 (3.972) nm.

360 MHz ¹H NMR (CDCl₃) δ 6.79 (s, 1H), 6.44 (s, 1H), 6.37 (t, 1H), 6.35 (d, 2H), 5.96 (s, 2H), 4.89 (d, 1H), 4.73 (q, 1H), 4.52–4.40 (m, 2H), 4.24 (d, 1H), 4.14 (dd, 1H), 3.97 (d, 1H), 3.78 (s, 6H), 3.62–3.53 (m, 2H), 3.47–3.41 (m, 1H), 3.32 (dd, 1H), 3.21 (dd, 1H), 3.17–3.10 (m, 1H), 3.04–2.97 (m, 1H), 2.68 (d, 1H, OH), 2.62 (d, 1H, OH), 1.35 (d, 3H).

mass spectrum (EI), m/e, 572.1903 (M+). C₂₉H₃₂O₁₂ requires 572.1894.

EXAMPLE 3

Etoposide-4'-(1-phenyl-1H-tetrazol-5-yl) ether (VIa)

tetrazol-5-yl) ether (480 mg, 0.655 mmol) in dry THF (10 ml) was slowly added via cannula over 5 min. The resulting dark blue solution was stirred at ca −70° C. for 3½ h and a solution of (1)-tartaric acid (1.10 g) in dry THF (12 ml) was added over 3 min. After 5 min at −78° C., glacial acetic acid (2 ml) was added and the mixture was stirred at −78° C. for 10 min, treated with CH₂Cl₂ (4 ml) and H₂O (2 ml), and allowed to warm to room temperature. The mixture was diluted with H₂O (125 ml) and extracted with CH₂Cl₂ (100 ml), 5% aqueous sodium bicarbonate (100 ml), H₂O (100 ml), and brine (100 ml), and dried (Na₂SO₄). Rotary evaporation gave the crude product as a 74:26 mixture of cis (picro) and trans lactone isomers (HPLC; 65:35 CH₃OH/H₂O; IBM C18 column). Preparative HPLC on silica gel using 4:96 CH₃OH/CH₂Cl₂ gave 65.1 mg of the pure trans lactone isomer as a colorless solid, in addition to 200 mg of the picro isomer. Data for the trans isomer product:

IR (KBr) 1775, 1603, 1545, 1506, 1486, 1237, 1131, 1098, 1078, 763 cm⁻¹.

360 MHz ¹H NMR (CDCl₃) δ 7.82 (d, 2H, J=7.9 Hz), 7.54–7.42 (m, 3H), 6.82 (s, 1H), 6.55 (s, 1H), 6.33 (s, 2H), 5.99 (d, 2H), 4.91 (d, 1H, J=3.4 Hz), 4.74 (q, 1H, J=5.0 Hz), 4.66–4.63 (m, 2H), 4.43 (dd, 1H), 4.24 (dd, 1H), 4.16 (dd, 1H, J=4.1 and 10.4 Hz), 3.74 (m, 1H), 3.66 (s, 6H), 3.57 (m, 1H), 3.43 (m, 1H), 3.34–3.27 (m,

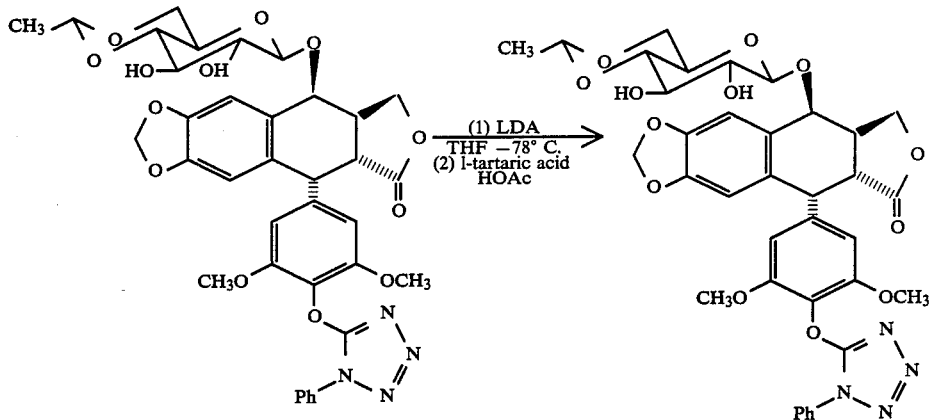

A magnetically stirred solution of diisopropylamine (0.48 g, 4.74 mmol) in dry THF (4 ml) under N₂ was cooled to −78° C. and n-butyllithium (1.6M in hexane; 2.6 ml, 4.16 mmol) was added via syringe. The mixture was allowed to warm to 0° C. over 15 min, recooled to −78° C., and a solution of the picro-4'-(1-phenyl-1H-

3H), 2.90–2.80 (m, 1H), 2.69 (br s, 1H, OH), 2.43 (br s, 1H, OH), 1.38 (d, 3H, J=5.0 Hz).

EXAMPLE 4

4'-Desmethoxyetoposide (IVa)

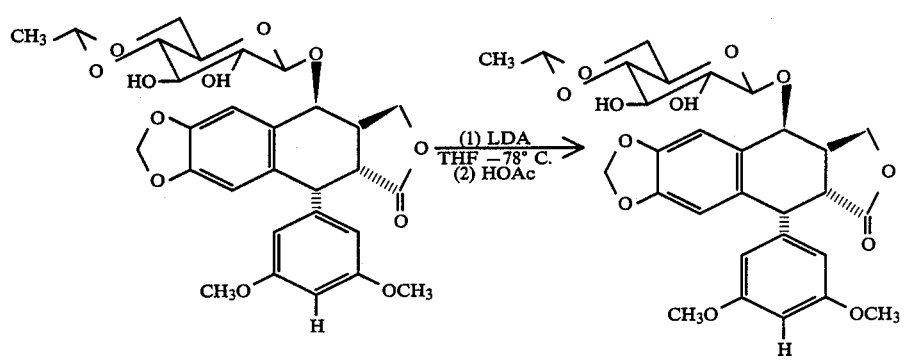

A magnetically stirred solution of diisopropylamine (0.30 ml, 2.14 mmol) in dry THF (1 ml) under $N_2$ was cooled to $-78°$ C and n-butyllithium (1.6M in hexane; 1.25 ml, 2.00 mmol) was added via syringe. The mixture was stirred at $-78°$ C. for 5 min, warmed to $-20°$ C. over 15 min, recooled to $-78°$ C., and a solution of picro-4'-desmethoxyetoposide (206.1 mg, 0.3599 mmol) in dry THF (2 ml) was slowly added followed by rinsing with dry THF (1 ml) to complete the transfer. The resulting light green solution was stirred at $-70°$ C. for 90 min and a solution of glacial acetic acid (0.75 ml) in dry THF (1 ml) was then slowly added via cannula to the dark blue reaction mixture. The resulting pale yellow solution was stirred at $-78°$ C. for 5 min, warmed to $0°$ C. over 15 min and diluted with $H_2O$ (25 ml) and extracted with $CH_2Cl_2$ (2×45 ml). The combined extracts were washed with $H_2O$ (20 ml) and brine (50 ml) and dried ($Na_2SO_4$). Rotary evaporation gave the crude product as a 73:27 mixture of cis (picro) and trans lactone isomers (HPLC; 65:35 $H_2O/CH_3CN$; C18 column; 14.3 min (picro) and 15.8 min (trans). Preparative TLC using 20 E. Merck 0.5 mm silica gel plates with 5% $MeOH/CH_2Cl_2$ provided 41.9 mg (21%) of the pure trans lactone isomer title product as a colorless solid, in addition to 116.0 mg (58%) of the picro isomer starting material which was recycled to give additional 4'-deshydroxyetoposide. Data for title product:

IR (KBr) 1777, 1597, 1485, 1233, 1206, 1158, 1039, 937, 701 cm$^{-1}$.

360 MHz $^1$H NMR (CDCl$_3$) δ6.77 (s, 1H), 6.50 (s, 1H), 6.27 (t, 1H, J=2.1 Hz), 6.18 (d, 2H, J=2.1 Hz), 5.95 (s, 2H), 4.85 (d, 1H, J=3.5 Hz), 4.73 (q, 1H, J=5.0 Hz), 4.63 (d, 1H, J=7.7 Hz), 4.58 (d, 1H, J=5.3 Hz), 4.38 (dd, 1H, J=9.1 and 10.3 Hz), 4.21–4.13 (m, 2H), 3.76–3.72 (m, 1H), 3.71 (s, 6H), 3.55 (m, 1H), 3.42 (m, 1H), 3.35–3.30 (m, 2H), 3.24 (dd, 1H, J=5.4 and 14.1 Hz), 2.97–2.88 (m, 1H), 2.66 (br s, 1H, OH), 2.36 (br s, 1H, OH), 1.37 (d, 3H, J=5.0 Hz).

EXAMPLE 5

4'-Deshydroxyetoposide

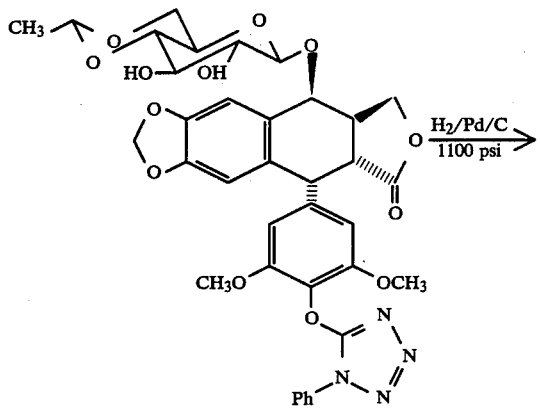

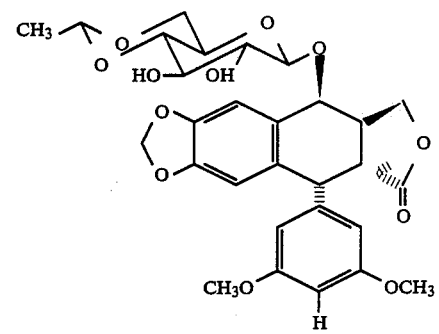

If the procedure of Example 2 is repeated with the picro-etoposide-4'-tetrazole ether replaced by an equivalent amount of trans-etoposide-4'-tetrazole ether VIa there is obtained the desired 4'-deshydroxyetoposide IVa.

EXAMPLE 6

Following the general procedure of Examples 1–5 but replacing the etoposide starting material in Example 1 with an equivalent amount of teniposide ($R^2$=H; $R^1$=2-thienyl) will give the corresponding products of formulae IV, V, VI and VII where $R^2$=H and $R^1$=2-thienyl.

EXAMPLE 7

Following the general procedures of Examples 1–5 but replacing the etoposide starting material in Example 1 with an equivalent amount of the starting materials shown below will produce the corresponding products of formulae IV, V, VI and VII wherein $R^2$ and $R^1$ are as defined below for starting material I.

STARTING MATERIAL

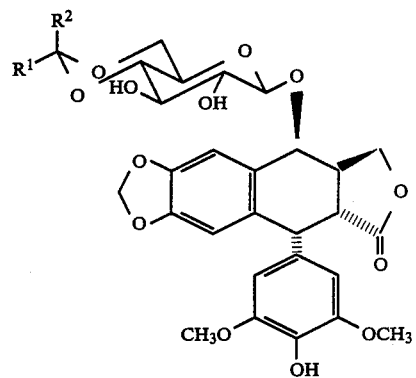

| Example No. | $R^2$ | $R^1$ |
|---|---|---|
| 7 a | H | $C_2H_5$ |
| 7 b | H | $(CH_3)_3CH$ |
| 7 c | H | $CH_3(CH_2)_2$ |
| 7 d | H | $C_2H_5CHCH_3$ |
| 7 e | H | $CH_3CHCH_2CH_3$ |
| 7 f | H | $(CH_3)_3C$ |
| 7 g | H | n-$C_7H_9$ |
| 7 h | H | cyclopentyl |
| 7 j | H | n-pentyl |
| 7 k | H | $C_6H_{11}$ |
| 7 l | H | $CH_3(CH_2)_2CH(CH_3)$ |

-continued

STARTING MATERIAL

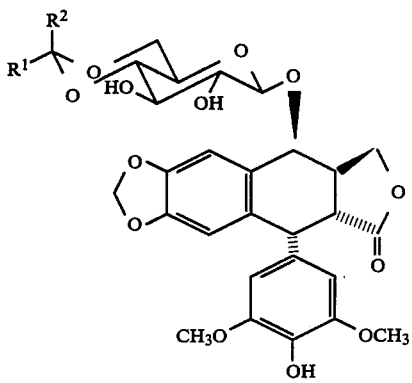

| Example No. | $R^2$ | $R^1$ |
|---|---|---|
| 7 m | H | (furyl structure) |
| 7 n | H | $C_6H_5$ |
| 7 o | H | o-$HOC_6H_4$ |
| 7 p | H | o-$MeC_6H_4$ |
| 7 q | H | p-$MeOC_6H_4$ |
| 7 r | H | o-$MeOC_6H_4$ |
| 7 s | H | p-$FC_6H_4$ |
| 7 t | H | m-$HOC_6H_4$ |
| 7 u | H | m-$MeOC_6H_4$ |
| 7 v | H | p-$HOC_6H_4$ |
| 7 x | H | p-$MeC_6H_4$ |
| 7 y | H | p-i-$PrC_6H_4$ |
| 7 z | H | (dimethoxyphenyl, $CH_3O$, $OCH_3$) |
| 7 aa | H | (methoxy/ethoxyphenyl, $CH_3O$, $OC_2H_5$) |
| 7 ab | H | (HO, $CH_3O$ phenyl) |
| 7 ac | H | $C_6H_5CH_2$ |
| 7 ad | H | $C_6H_5(CH_2)_2$ |
| 7 ae | H | 1-naphthyl |
| 7 af | $CH_3$ | $CH_3$ |
| 7 ag | $C_2H_5$ | $CH_3$ |
| 7 ah | | $CH_2(CH_2)_2CH_3$ |
| 7 ai | | $CH_2(CH_2)_3CH_3$ |

We claim:
1. A compound having the formula

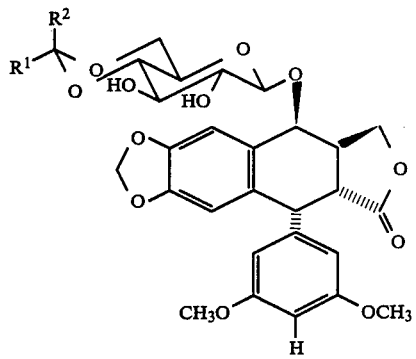

wherein $R^2$ is hydrogen and $R^1$ is selected from the group consisting of $C_1$-$C_{10}$ alkyl, $C_2$-$C_{10}$ alkenyl, $C_3$-$C_7$ cycloalkyl, furyl, thienyl, pyridyl, pyrrolyl, $C_6$-$C_{10}$ aryl and $C_7$-$C_{14}$ aralkyl, said aryl and aralkyl rings being unsubstituted or substituted by one or more substituents selected from the group consisting of halo, $C_1$-$C_4$ alkyl, nitro, hydroxy, $C_1$-$C_4$ alkoxy, $C_1$-$C_4$ alkanoyloxy, cyano, amino, $C_1$-$C_4$ alkylamino, di($C_1$-$C_4$) alkylamino, carboxy, $C_1$-$C_4$ alkylthio, mercapto, $C_2$-$C_4$ alkenoylamino, $C_{1-4}$alkanoyl, $C_2$-$C_4$ alkenyl and carbamoyl; or $R^1$ and $R^2$ are each $C_1$-$C_{10}$ alkyl; or $R^1$ and $R^2$ and the carbon atom to which they are attached join to form a $C_5$-$C_6$ cycloalkyl group.

2. A compound according to claim 1 wherein $R^2$ is hydrogen and $R^1$ is methyl, phenyl or 2-thienyl.

3. A compound according to claim 1 wherein $R^2$ is hydrogen and $R^1$ is 2-methyl.

4. An intermediate having the formula

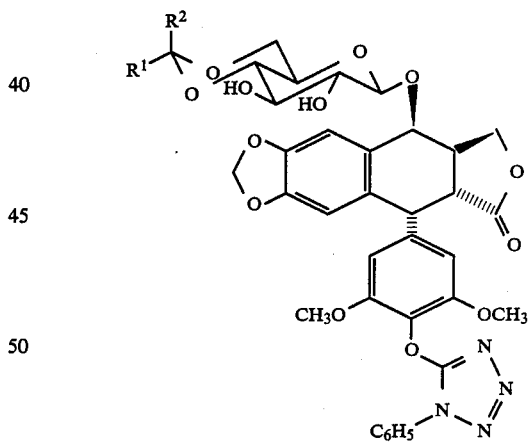

wherein $R^2$ is hydrogen and $R^1$ is selected from the group consisting of $C_1$-$C_{10}$ alkyl, $C_2$-$C_{10}$ alkenyl, $C_3$-$C_7$ cycloalkyl, furyl, thienyl, pyridyl, pyrrolyl, $C_6$-$C_{10}$ aryl and $C_7$-$C_{14}$ aralkyl, said aryl and aralkyl rings being unsubstituted or substituted by one or more substituents selected from the group consisting of halo, $C_1$-$C_4$ alkyl, nitro, hydroxy, $C_1$-$C_4$ alkoxy, $C_1$-$C_4$ alkanoyloxy, cyano, amino, $C_1$-$C_4$ alkylamino, di($C_1$-$C_4$)alkylamino, carboxy, $C_1$-$C_4$ alkylthio, mercapto, $C_2$-$C_4$ alkenoylamino, $C_1$-$C_4$ alkanoyl, $C_2$-$C_4$ alkenyl and carbamoyl; or $R^1$ and $R^2$ are each $C_1$-$C_{10}$ alkyl; or $R^1$ and $R^2$ and the carbon atom to which they are attached join to form a $C_5$-$C_6$ cycloalkyl group.

5. An intermediate according to claim 4 wherein $R^2$ is hydrogen and $R^1$ is methyl, phenyl or 2-thienyl.

6. The intermediate according to claim 4 wherein $R^2$ is hydrogen and $R^1$ is methyl.

7. An intermediate having the formula

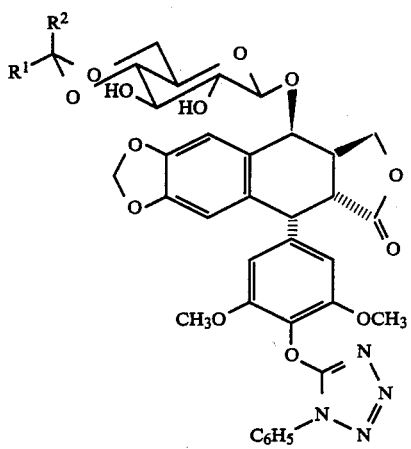

wherein $R^2$ is hydrogen and $R^1$ is selected from the group consisting of $C_1$-$C_{10}$ alkyl, $C_2$-$C_{10}$ alkenyl, $C_3$-$C_7$ cycloalkyl, furyl, thienyl, pyridyl, pyrrolyl, $C_6$-$C_{10}$ aryl and $C_7$-$C_{14}$ aralkyl, said aryl and aralkyl rings being unsubstituted or substituted by one or more substituents selected from the group consisting of halo, $C_1$-$C_4$ alkyl, nitro, hydroxy, $C_1$-$C_4$ alkoxy, $C_1$-$C_4$ alkanoyloxy, cyano, amino, $C_1$-$C_4$ alkylamino, di($C_1$-$C_4$)alkylamino, carboxy, $C_1$-$C_4$ alkylthio, mercapto, $C_2$-$C_4$ alkenoylamino, $C_1$-$C_4$ alkanoyl, $C_2$-$C_4$ alkenyl and carbamoyl; or $R^1$ and $R^2$ are each $C_1$-$C_{10}$ alkyl; or $R^1$ and $R^2$ and the carbon atom to which they are attached join to form a $C_5$-$C_6$ cycloalkyl group.

8. An intermediate according to claim 7 wherein $R^2$ is hydrogen and $R^1$ is methyl, phenyl or 2-thienyl.

9. The intermediate according to claim 7 wherein $R^2$ is hydrogen and $R^1$ is methyl.

10. An intermediate having the formula

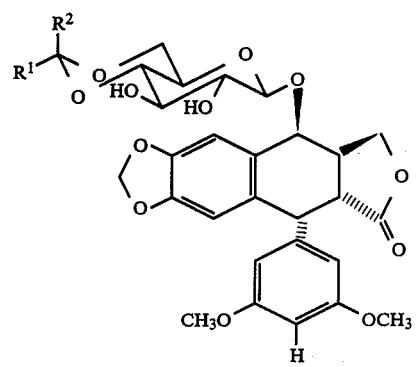

wherein $R^2$ is hydrogen and $R^1$ is selected from the group consisting of $C_1$-$C_{10}$ alkyl, $C_2$-$C_{10}$ alkenyl, $C_3$-$C_7$ cycloalkyl, furyl, thienyl, pyridyl, pyrrolyl, $C_6$-$C_{10}$ aryl and $C_7$-$C_{14}$ aralkyl, said aryl and aralkyl rings being unsubstituted or substituted by one or more substituents selected from the group consisting of halo, $C_1$-$C_4$ alkyl, nitro, hydroxy, $C_1$-$C_4$ alkoxy, $C_1$-$C_4$ alkanoyloxy, cyano, amino, $C_1$-$C_4$ alkylamino, di($C_1$-$C_4$)alkylamino, carboxy, $C_1$-$C_4$ alkylthio, mercapto, $C_2$-$C_4$ alkenoylamino, $C_1$-$C_4$ alkanoyl, $C_2$-$C_4$ alkenyl and carbamoyl; or $R^1$ and $R^2$ are each $C_1$-$C_{10}$ alkyl; or $R^1$ and $R^2$ and the carbon atom to which they are attached join to form a $C_5$-$C_6$ cycloalkyl group.

11. An intermediate according to claim 10 wherein $R^2$ is hydrogen and $R^1$ is methyl, phenyl or 2-thienyl.

12. The intermediate according to claim 10 wherein $R^2$ is hydrogen and $R^1$ is methyl.

* * * * *